United States Patent
Cai et al.

(10) Patent No.: US 10,326,466 B2
(45) Date of Patent: Jun. 18, 2019

(54) ANALOG TO DIGITAL CONVERTER

(71) Applicant: Huawei Technologies Co., Ltd., Shenzhen (CN)

(72) Inventors: Yu Cai, Shenzhen (CN); Chunhui Zhang, Wuhan (CN); Jifang He, Wuhan (CN)

(73) Assignee: HUAWEI TECHNOLOGIES CO., LTD., Shenzhen (CN)

( * ) Notice: Subject to any disclaimer, the term of this patent is extended or adjusted under 35 U.S.C. 154(b) by 210 days.

(21) Appl. No.: 15/637,846

(22) Filed: Jun. 29, 2017

(65) Prior Publication Data

US 2017/0302290 A1    Oct. 19, 2017

Related U.S. Application Data

(63) Continuation of application No. PCT/CN2014/095625, filed on Dec. 30, 2014.

(51) Int. Cl.
*G02F 7/00* (2006.01)
*H03M 1/14* (2006.01)
(Continued)

(52) U.S. Cl.
CPC ........ *H03M 1/146* (2013.01); *G01N 15/1436* (2013.01); *G01N 15/1459* (2013.01); *G02F 7/00* (2013.01); *G11C 27/02* (2013.01); *G11C 27/024* (2013.01); *G11C 27/026* (2013.01); *H03K 17/06* (2013.01)

(58) Field of Classification Search
CPC ...................................................... G02F 7/00
See application file for complete search history.

(56) References Cited

U.S. PATENT DOCUMENTS

| 4,712,089 A | 12/1987 | Verber |
| 5,010,346 A | 4/1991 | Hamilton et al. |

(Continued)

FOREIGN PATENT DOCUMENTS

| CN | 1635417 A | 7/2005 |
| CN | 1862355 A | 11/2006 |

(Continued)

OTHER PUBLICATIONS

B. Jalali et al., "Optical Folding-Flash Analog-to-Digital Converter with Analog Encoding", Optics Letters, vol. 20, No. 18, Sep. 15, 1995, pp. 1901-1903.

(Continued)

*Primary Examiner* — Patrick O Neill
(74) *Attorney, Agent, or Firm* — Slater Matsil, LLP (57) ABSTRACT

The present embodiments provide an analog to digital converter, including a beam splitter, M photodetectors, M amplifier modules, and an encoder. Each output end of the beam splitter is corresponding to an input end of a photodetector, an output end of each photodetector is connected to an input end of an amplifier module, and an output end of each amplifier module is connected to an input end of the encoder. The beam splitter splits an inputted analog optical signal into M optical signals, outputs each optical signal to a corresponding photodetector to convert each optical signal into a current signal, inputs each current signal to a corresponding amplifier module to generate an output voltage, and outputs the output voltage to a corresponding input end of the encoder.

20 Claims, 6 Drawing Sheets

(51) Int. Cl.
  *G01N 15/14* (2006.01)
  *G11C 27/02* (2006.01)
  *H03K 17/06* (2006.01)

(56) References Cited

U.S. PATENT DOCUMENTS

| | | |
|---|---|---|
| 5,381,148 A | 1/1995 | Mueck et al. |
| 6,118,396 A | 9/2000 | Song |
| 6,326,910 B1 | 12/2001 | Hayduk et al. |
| 7,809,216 B2 | 10/2010 | Cox, III |
| 8,263,928 B1 | 9/2012 | Efimov |
| 8,269,658 B1 | 9/2012 | Pace et al. |
| 2011/0234436 A1 | 9/2011 | Bogoni et al. |
| 2012/0269514 A1 | 10/2012 | Nedovic |

FOREIGN PATENT DOCUMENTS

| | | |
|---|---|---|
| CN | 101290456 A | 10/2008 |
| CN | 102799045 A | 11/2012 |
| JP | S5744130 A | 3/1982 |
| JP | S61282826 A | 12/1986 |
| JP | 2007024924 A | 2/2007 |
| JP | 2012231461 A | 11/2018 |

OTHER PUBLICATIONS

Phillip E. Pace et al., "High-Resolution Encoding Process for an Integrated Optical Analog-to-Digital Converter", Optical Engineering, vol. 33, No. 8, Aug. 1994, pp. 2638-2645.

ANALOG TO DIGITAL CONVERTER

CROSS-REFERENCE TO RELATED APPLICATIONS

This application is a continuation of International Application No. PCT/CN2014/095625, filed on Dec. 30, 2014, the disclosure of which is hereby incorporated by reference in its entirety.

TECHNICAL FIELD

Embodiments of the present invention relate to the field of communications technologies, and in particular, to an analog to digital converter.

BACKGROUND

A conventional analog to digital converter (ADC) circuit generally includes two parts: one part is a sampling head, that is, a sample-and-hold circuit (namely, the so-called Switch-Cap circuit, also referred to as a sample-and-hold device). The hold circuit generally includes a metal-oxide semiconductor (MOS for short) switch and a capacitor, and is used to implement a sample-and-hold function. A reason for using the sample-and-hold circuit is that when analog to digital (A/D) conversion is performed on an analog signal, a particular conversion time is required from a conversion start to digital signal output upon a conversion end. In this conversion time, the analog signal needs to remain unchanged. If the analog signal changes, conversion precision cannot be ensured. Especially when the inputted analog signal has a high frequency, a large conversion error is caused. To resolve this problem, a level of the inputted signal needs to be held when the A/D conversion starts, and a change of the inputted signal needs to be tracked after the A/D conversion ends. The sample-and-hold circuit is equivalent to an "analog signal memory" in a hold phase. The inputted signal is sampled and held, and is compared with different thresholds in a comparator, and information about different bits may be obtained. This is a principle of a common ADC.

Figure 1:
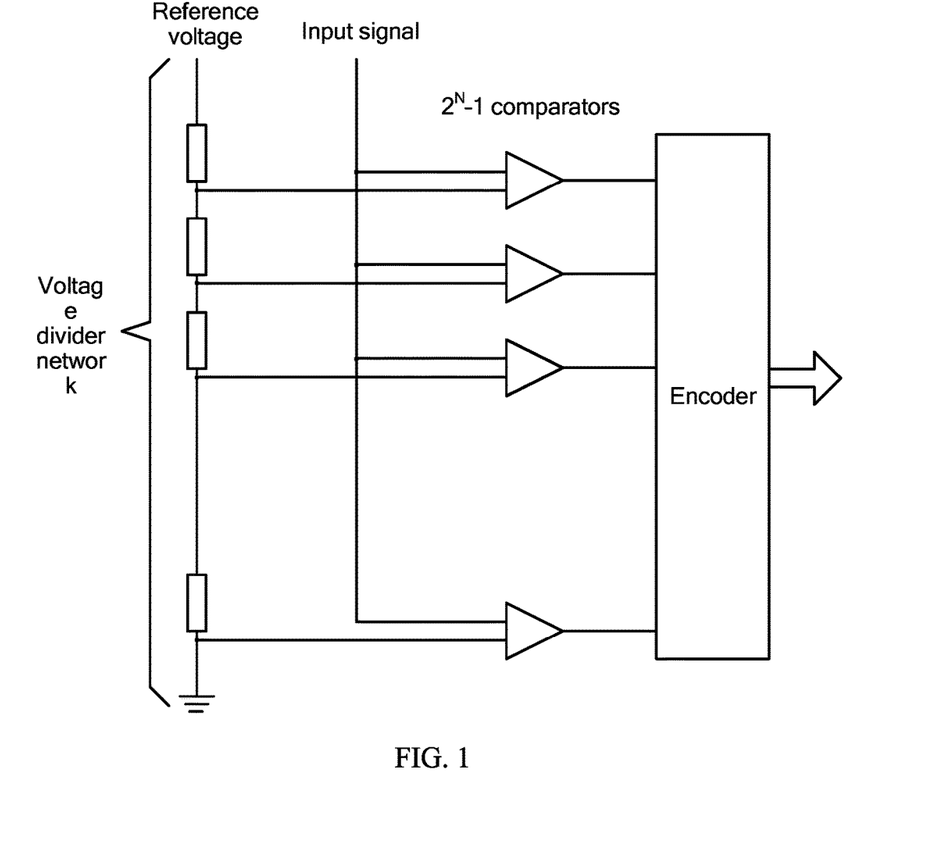
FIG. 1 is a schematic structural diagram of an analog to digital converter in the prior art.

Specifically, after sampling and holding the inputted signal, the sampling head inputs the inputted signal to the comparator. The comparator needs to complete comparison of multiple bits in a single sampling clock. As shown in FIG. 1, FIG. 1 is an architecture of an existing high-speed ADC, including a voltage divider network, a comparator, and an encoder. Specifically, if the existing high-speed ADC is an N-bit precision ADC, the voltage divider network generally needs to include $2^N$ resistors of an equal resistance, $2^N-1$ reference voltages are generated on the voltage divider network, and accordingly $2^N-1$ comparators (triangle symbols in the figure) are required. An inputted signal (sampled) on which A/D conversion needs to be performed gains access to an input end of each of the $2^N-1$ comparators, and the $2^N-1$ reference voltages generated on the voltage divider network separately gain access to the other input end of each of the $2^N-1$ comparators, so as to separately compare the inputted signal with the $2^N-1$ reference voltages. The two input ends of each comparator are respectively one positive and one negative. If positive input is greater than negative input, 1 is output. If positive input is not greater than negative input, 0 is output. A result obtained by the comparator is outputted to the encoder. The encoder obtains an N-bit binary number by calculation which indicates a value of the inputted signal. At this point, the analog to digital conversion is completed.

Though the architecture of the existing ADC shown in FIG. 1 is the fastest in current electrical ADC solutions, a rate of a sampling head is very limited because the sampling head in the prior aft is inherently limited by an electrical signal (for example, a capacitor), and a rate requirement in some scenarios cannot be met (for example, in a radio frequency signal processing scenario). Therefore, to improve a sampling rate, multiple sampling heads have to be used for parallel processing in some scenarios. For example, four sampling heads sometimes need to be set in front of a comparator circuit for parallel processing in an ADC circuit of a GHz magnitude. In addition, for some scenarios with a higher rate requirement, such as a 5 GHz scenario, a 10 GHz scenario, or a scenario with an even higher requirement, the foregoing conventional electrical ADC cannot meet a requirement. Therefore, how to further improve an ADC rate is a problem that urgently needs to be resolved, so as to meet a higher rate requirement in an application scenario.

SUMMARY

Embodiments of the present invention provide an analog to digital converter, which can improve a conversion rate of the analog to digital converter.

According to a first aspect, an analog to digital converter is provided, where the analog to digital converter includes a beam splitter, M photodetectors, M amplifier modules corresponding to the M photodetectors, and an encoder. Each output end of the beam splitter is corresponding to an input end of a photodetector, an output end of each photodetector is connected to an input end of an amplifier module, and an output end of each amplifier module is connected to an input end of the encoder. The beam splitter is configured to split an inputted analog optical signal into M optical signals, and output each optical signal to a corresponding photodetector. The photodetector is configured to convert the inputted optical signal into a current signal, and input the current signal to a corresponding amplifier module. The amplifier module is configured to generate an output voltage according to the inputted current signal, and output the output voltage to a corresponding input end of the encoder. The encoder is configured to compare inputted M output voltages with a decision voltage, so as to obtain M decision results, and generate a digital signal according to the M decision results. Power of the M optical signals decreases progressively from a first optical signal to an $M^{th}$ optical signal according to a first preset proportion, conversion efficiency of the M photodetectors decreases progressively from a first photodetector to an $M^{th}$ photodetector according to a second preset proportion, and amplification multiples of the M amplifier modules decrease progressively from a first amplifier module to an $M^{th}$ amplifier module according to a third preset proportion, so that the M output voltages that are inputted to the encoder decrease progressively from a first output voltage to an $M^{th}$ output voltage according to a fourth preset proportion, or the analog to digital converter is an N-bit precision analog to digital converter, M is equal to $2^N-1$, the digital signal is of N bits, and M and N are positive integers.

According to a second aspect, an analog to digital converter is provided, where the analog to digital converter includes a beam splitter, M photodetectors, M amplifier modules corresponding to the M photodetectors, M deciders corresponding to the M amplifier modules, and an encoder.

Each output end of the beam splitter is corresponding to an input end of a photodetector, an output end of each photodetector is connected to an input end of an amplifier module, an output end of each amplifier module is connected to a decider, and an output end of each decider is connected to an input end of the encoder. The beam splitter is configured to split an inputted analog optical signal into M optical signals, and output each optical signal to a corresponding photodetector, where power of the M optical signals is equal. The photodetector is configured to convert the inputted optical signal into a current signal, and input the current signal to a corresponding amplifier module, where conversion efficiency of the M photodetectors is equal. The amplifier module is configured to generate an output voltage according to the inputted current signal, and output the output voltage to a corresponding decider. Amplification multiples of the M amplifier modules are equal. Decision voltages are set in the M deciders, the decision voltages of the M deciders progressively decrease from a first decider to an $M^{th}$ decider according to a preset proportion, and the decider is configured to compare the inputted output voltage with a decision voltage of the decider, so as to obtain a decision result, and transmit the decision result to a corresponding input end of the encoder. The encoder is configured to generate a digital signal according to M decision results. The analog to digital converter is an N-bit precision analog to digital converter, $M=2^N-1$, the digital signal is of N bits, and M and N are positive integers.

BRIEF DESCRIPTION OF THE DRAWINGS

To describe the technical solutions in the embodiments of the present invention more clearly, the following briefly describes the accompanying drawings required for describing the embodiments. Apparently, the accompanying drawings in the following description show some embodiments of the present invention, and a person of ordinary skill in the art may still derive other drawings from these accompanying drawings without creative efforts.

DETAILED DESCRIPTION OF ILLUSTRATIVE EMBODIMENTS

To make the objectives, technical solutions, and advantages of the embodiments of the present invention clearer, the following clearly describes the technical solutions in the embodiments of the present invention with reference to the accompanying drawings in the embodiments of the present invention. Apparently, the described embodiments are some but not all of the embodiments of the present invention. All other embodiments obtained by a person of ordinary skill in the art based on the embodiments of the present invention without creative efforts shall fall within the protection scope of the present embodiments.

An embodiment of the present invention provides an analog to digital converter. The analog to digital converter includes a beam splitter, M photodetectors, M amplifier modules corresponding to the M photodetectors, and an encoder; where each output end of the beam splitter is corresponding to an input end of a photodetector, an output end of each photodetector is connected to an input end of an amplifier module, and an output end of each amplifier module is connected to an input end of the encoder.

The beam splitter is configured to split an inputted analog optical signal into M optical signals, and output each optical signal to a corresponding photodetector.

The photodetector is configured to convert the inputted optical signal into a current signal, and input the current signal to a corresponding amplifier module.

The amplifier module is configured to generate an output voltage according to the inputted current signal, and output the output voltage to a corresponding input end of the encoder.

The encoder is configured to compare inputted M output voltages with a decision voltage, so as to obtain M decision results, and generate a digital signal according to the M decision results.

At least one of the following is included: power of the M optical signals decreases progressively from a first optical signal to an $M^{th}$ optical signal according to a first preset proportion, conversion efficiency of the M photodetectors decreases progressively from a first photodetector to an $M^{th}$ photodetector according to a second preset proportion, and amplification multiples of the M amplifier modules decrease progressively from a first amplifier module to an $M^{th}$ amplifier module according to a third preset proportion, so that the M output voltages that are inputted to the encoder decrease progressively from a first output voltage to an $M^{th}$ output voltage according to a fourth preset proportion.

It may be understood that at least one of the foregoing manners may be selected, or a combination of several manners may be selected, so that the M output voltages that are inputted to the encoder decrease progressively from the first output voltage to the $M^{th}$ output voltage according to the fourth preset proportion. It should be understood that, if a manner is selected from the foregoing manners for execution, other coefficients of components that belong to a same type should be equal, and the first preset proportion, the second preset proportion, or the third preset proportion is equal to the fourth preset proportion in this case. For example, if the amplification multiples of the M amplifier modules decrease progressively from the first amplifier module to the $M^{th}$ amplifier module according to the third preset proportion, the power of the M optical signals is equal, and the conversion efficiency of the M photodetectors is equal, and the fourth preset proportion is equal to the third preset proportion in this case, and so on. If at least two manners are selected from the foregoing manners, other coefficients of components that belong to a same type except the at least two manners should be equal. For example, that the power of the M optical signals decrease progressively from the first optical signal to the $M^{th}$ optical signal according to the first preset proportion, and the conversion efficiency of the M photodetectors decreases progressively from the first photodetector to the $M^{th}$ photodetector according to the second preset proportion are selected, the amplification multiples of the M amplifier modules are equal in this case, and current signals outputted by the M photodetectors should decrease progressively according to the fourth preset proportion. Because the amplification multiples of the M amplifier modules are equal, the M output voltages that are inputted to the encoder decrease progressively from the first output voltage to the $M^{th}$ output voltage according to the fourth preset proportion.

The analog to digital converter is an N-bit precision analog to digital converter, M is equal to $2^N-1$, the digital signal is of N bits, and M and N are positive integers.

An embodiment of the present invention provides another analog to digital converter. A decider may be disposed between each amplifier and an input end of an encoder corresponding to the amplifier. The analog to digital converter includes a beam splitter, M photodetectors, M amplifier modules corresponding to the M photodetectors, M deciders corresponding to the M amplifier modules, and an encoder. Each output end of the beam splitter is corresponding to an input end of a photodetector, an output end of each photodetector is connected to an input end of an amplifier module, an output end of each amplifier module is connected to a decider, and an output end of each decider is connected to an input end of the encoder.

The beam splitter is configured to split an inputted analog optical signal into M optical signals, and output each optical signal to a corresponding photodetector, where power of the M optical signals is equal.

The photodetector is configured to convert the inputted optical signal into a current signal, and input the current signal to a corresponding amplifier module, where conversion efficiency of the M photodetectors is equal.

The amplifier module is configured to generate an output voltage according to the inputted current signal, and output the output voltage to a corresponding decider; where amplification multiples of the M amplifier modules are equal.

Decision voltages are set in the M deciders, the decision voltages of the M deciders progressively decrease from a first decider to an $M^{th}$ decider according to a preset proportion, and the decider is configured to compare the inputted output voltage with a decision voltage of the decider, so as to obtain a decision result, and transmit the decision result to a corresponding input end of the encoder.

The encoder is configured to generate a digital signal according to M decision results.

The analog to digital converter is an N-bit precision analog to digital converter, M=$2^N-1$, the digital signal is of N bits, and M and N are positive integers.

Figure 2:
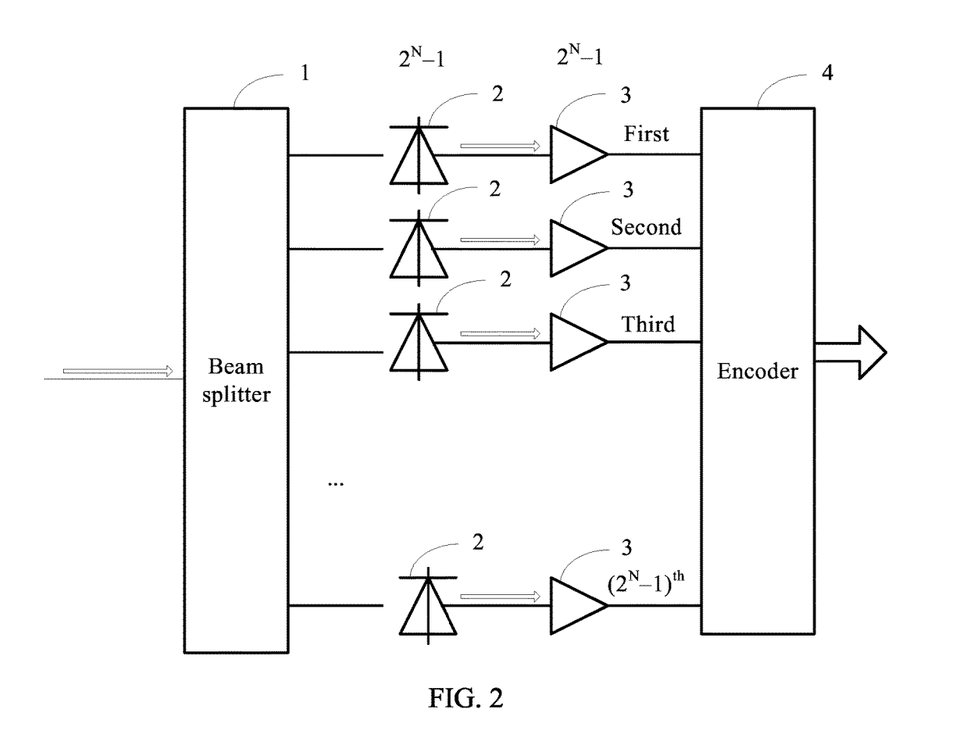
FIG. 2 is a schematic structural diagram of an analog to digital converter according to an embodiment of the present invention.

To make a person skilled in the art more clearly understand the technical solutions provided in the embodiments of the present invention, the following describes in detail, by using a specific embodiment, the analog to digital converter according to the embodiments of the present invention. As shown in FIG. 2, the analog to digital converter includes: a beam splitter 1, M photodetectors 2, M amplifier modules 3 corresponding to the M photodetectors 2, and an encoder 4, where each output end of the beam splitter 1 is corresponding to an input end of a photodetector 2, an output end of each photodetector 2 is connected to an input end of an amplifier module 3, and an output end of each amplifier module 3 is connected to an input end of the encoder 4, and M is a positive integer.

Figure 3A:
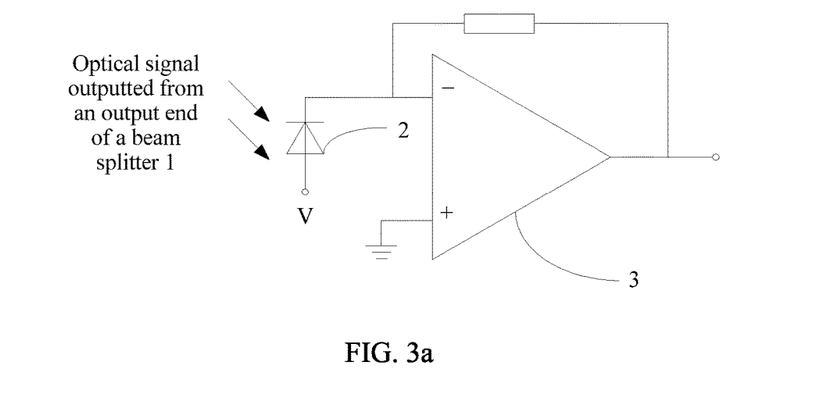
FIG. 3a is a schematic connection diagram of a beam splitter, a photodetector, and an amplifier module in an analog to digital converter according to an embodiment of the present invention.
Figure 3B:
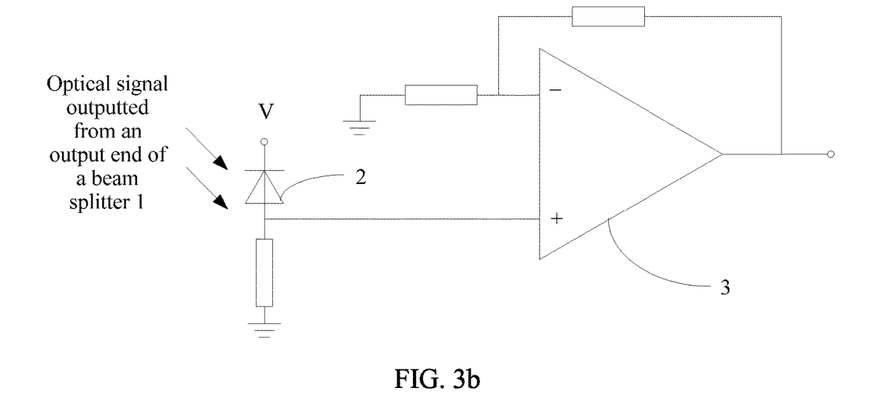
FIG. 3b is another schematic connection diagram of a beam splitter, a photodetector, and an amplifier module in an analog to digital converter according to an embodiment of the present invention.

That each output end of the beam splitter 1 is corresponding to an input end of a photodetector 2 may be understood as that each output end of the beam splitter 1 is not physically connected to the input end of the photodetector 2, and an optical signal outputted from each output end of the beam splitter 1 directly irradiates the photodetector 2. For example, a manner of connecting the beam splitter 1, a photodetector 2, and an amplifier module 3 may be as that shown in FIG. 3a or FIG. 3b. V in FIG. 3a or FIG. 3b indicates a bias voltage provided to the photodetector 2.

In various embodiments of the present invention, the amplifier module 3 may be a transimpedance amplifier, or may be another component with functions of converting a current into a voltage and signal amplification.

In a first implementation manner, a comparator function may be implemented by using the M photodetectors 2 of same conversion efficiency and the M amplifier modules 3 of different amplification multiples.

Specifically, an analog optical signal on which A/D conversion needs to be performed is directly inputted to an input end of the beam splitter 1. The beam splitter 1 is configured to split the inputted analog optical signal into M optical signals, and output the M optical signals to the corresponding photodetectors 2. Power of the M optical signals outputted by the beam splitter 1 is equal.

The photodetector 2 is configured to convert the inputted optical signal into a current signal, and input the current signal to a corresponding amplifier module 3. Strength of M current signals outputted by the M photodetectors 2 is equal.

The amplifier module 3 is configured to generate an output voltage according to the inputted current signal, and output the output voltage to a corresponding input end of the encoder. Amplification multiples of the M amplifier modules 3 decrease progressively from a first amplifier module 3 to an $M^{th}$ amplifier module 3 according to a preset proportion.

The encoder 4 is configured to compare inputted M output voltages with a decision voltage, and output a digital signal according to comparison results.

For example, the analog to digital converter is an N-bit precision analog to digital converter, M=$2^N-1$, and N is a positive integer. The analog to digital converter provided in the foregoing first implementation manner is described in detail by using the following example.

After the analog optical signal is inputted to the beam splitter 1, the beam splitter 1 splits the analog optical signal into the $2^N-1$ optical signals of equal power, and separately outputs the $2^N-1$ optical signals to the $2^N-1$ photodetectors 2. The beam splitter 1 may be implemented by using a silicon waveguide or a silicon dioxide waveguide, or may be implemented in another manner.

Because the conversion efficiency of the $2^N-1$ photodetectors 2 is identical, the strength of the $2^N-1$ current signals obtained by conversion by the $2^N-1$ photodetectors 2 according to the $2^N-1$ optical signals is the same. It is assumed that the intensity of the $2^N-1$ current signals are I, and the photodetector in this embodiment may be a photodiode.

An amplification multiple of an amplifier module 3 may be understood as a ratio of an output voltage of the amplifier module 3 to an inputted photocurrent signal. The amplification multiples of the $2^N-1$ amplifier modules 3 may be set to be decreased progressively according to the preset proportion. This, for example, may include:

An amplification multiple of an $n^{th}$ (of the $2^N-1$ amplifier modules 3 shown in FIG. 2, the first amplifier module 3 to the $(2^N-1)^{th}$ amplifier module 3 are respectively arranged from top to bottom along a vertical direction shown in FIG.

2) amplifier module 3 of the $2^N-1$ amplifier modules 3 is $\Delta(n-k)$, where $\Delta$ is one $(2^N)^{th}$ of a reference voltage, k is a coefficient, k is a positive number, n is a positive integer, an initial value of n is 1, and n is less than or equal to $2^N-1$. That is, the amplification multiples of the $2^N-1$ amplifier modules 3 are $\Delta/(1-k)$, $\Delta/(2-k)$, $\Delta/(3-k)$, . . . , $\Delta/(2^N-1-k)$ respectively. Optionally, if the amplifier module 3 is a transimpedance amplifier, the amplification multiples of the amplifier module 3 may be adjusted by changing a resistance of a bridging resistor.

After the $2^N-1$ photodetectors 2 input the $2^N-1$ current signals of the strength I to the foregoing $2^N-1$ amplifier modules 3, the $2^N-1$ output voltages outputted by the $2^N-1$ amplifier modules 3 are $\Delta I(1-k)$, $\Delta I(2-k)$, $\Delta I/(3-k)$, . . . , and $\Delta I(2^N-1-k)$ respectively, and then the $2^N-1$ amplifier modules 3 separately input the $2^N-1$ output voltages to the encoder 4.

A decision voltage is preset in the encoder 4. For example, the decision voltage may be $\Delta I(1-k)$. It should be noted that a decision voltage of an encoder is generally determined. Therefore, in actual solution implementation, an amplification multiple of an amplifier module is set according to the decision voltage of the encoder. That is, the decision voltage $\Delta I/k$ in this embodiment is known, and the amplification multiples of the $2^N-1$ amplifier modules 3 are set according to the decision voltage $\Delta I/k$.

The encoder separately (concurrently) compares the $2^N-1$ output voltages with the decision voltage, and obtains the decision results of $2^N-1$ input ends of the encoder 4 according to the comparison results.

Specifically, if an output voltage of an $n^{th}$ amplifier module inputted from an $n^{th}$ input end is greater than or equal to the decision voltage, it is determined that a decision result of the $n^{th}$ input end is a first value. If an output voltage of an $n^{th}$ amplifier module is less than the decision voltage, it is determined that input of the $n^{th}$ input end is a second value. The $n^{th}$ amplifier module is any one of the $2^N-1$ amplifier modules. The $n^{th}$ input end is an input end corresponding to the $n^{th}$ amplifier module. The first value and the second value may be 1 and 0 respectively.

The encoder 4 obtains the N-bit digital signal by calculation by using the decision results of the $2^N-1$ input ends and outputs the N-bit digital signal.

Specifically, the encoder may count a quantity of 1 in the $2^N-1$ decision results, and generate the N-bit digital signal according to the quantity.

For example, in this embodiment, it is set that k=0, and the decision voltage is $\Delta I$, the amplification multiples of the $2^N-1$ amplifier modules are $\Delta$, $\Delta/2$, $\Delta/3$, . . . , and $\Delta/2^N-1$ respectively, and the $2^N-1$ output voltages outputted by the $2^N-1$ amplifier modules are $\Delta I$, $\Delta I/2$, $\Delta I/3$, . . . , and $\Delta I(2^N-1)$ respectively. The $2^N-1$ output voltages $\Delta I$, $\Delta I/2$, $\Delta I/3$, . . . , and $\Delta I/(2^N-1)$ are separately compared with $\Delta I$, and it may be concluded that the output voltage of the first amplifier module is not less than the decision voltage. Therefore, the obtained decision results of the $2^N-1$ input ends of the encoder 4 are 1, 0, 0, 0, . . . , and 0 respectively. In this case, the quantity of 1 in the $2^N-1$ decision results is 1, and the N-bit digital signal that is obtained by the encoder by calculation according to the $2^N-1$ input values and that is outputted by the encoder is 00 . . . 001.

If the inputted analog optical signal changes, and it is assumed that an intensity of a photocurrent signal generated by each photodetector changes to 2I, the output voltage of the first amplifier module and an output voltage of a second amplifier module are not less than a decision level. In this case, the quantity of 1 in the $2^N-1$ decision results is 2, and the N-bit digital signal outputted by the encoder 4 is 00 . . . 010.

In addition, k may be another value. For example, it may be set that k=0.5, and the decision voltage is $\Delta I/0.5$, and the amplification multiples of the $2^N-1$ amplifier modules are $\Delta/0.5$, $\Delta/1.5$, $\Delta/2.5$, . . . , and $\Delta(2^N-1.5)$ respectively. In addition, k may be another value, for example, 0.9, or 0.001. A specific value of k needs to be adjusted according to power of the inputted analog optical signal, so as to select a proper decision voltage for the analog optical signal on which A/D conversion needs to be performed, thereby ensuring a more accurate decision. A step of converting the analog optical signal into a digital signal when k is another value is the same as that when k=0, and details are not described.

An analog optical signal can be directly converted into a digital signal by using the foregoing method.

In a second implementation manner, a comparator function may be implemented by using the M photodetectors 2 of different conversion efficiency and the M amplifier modules 3 of a same amplification multiple, where M is a positive integer.

Specifically, an analog optical signal on which analog to digital (A/D) conversion needs to be performed is directly inputted to an input end of the beam splitter 1. The beam splitter 1 is configured to split the inputted analog optical signal into multiple optical signals corresponding to the M photodetectors 2, and output the multiple optical signals to the M photodetectors 2. Power of the M optical signals is equal.

The photodetector 2 is configured to convert the inputted optical signal into a current signal, and input the current signal to a corresponding amplifier module 3. Strength of M current signals that are outputted by the M photodetectors 2 decreases progressively from a first current signal to an $M^{th}$ current signal according to a preset proportion.

The amplifier module 3 is configured to generate an output voltage according to the inputted current signal, and output the output voltage to a corresponding input end of the encoder. Amplification multiples of the M amplifier modules 3 are equal.

The encoder 4 is configured to compare M output voltages with a decision voltage, and output a digital signal according to comparison results.

For example, the analog to digital converter is an N-bit precision analog to digital converter, $M=2^N-1$, and N is a positive integer. The analog to digital converter provided in the foregoing second implementation manner is described in detail by using the following example.

After the analog optical signal is inputted to the beam splitter 1, the beam splitter 1 splits the analog optical signal into the $2^N-1$ optical signals of equal power, and separately outputs the $2^N-1$ optical signals to the $2^N-1$ photodetectors 2. The beam splitter 1 may be implemented by using a silicon waveguide or a silicon dioxide waveguide, or may be implemented in another manner.

The $2^N-1$ photodetectors 2 convert the $2^N-1$ optical signals into the $2^N-1$ current signals, and output the $2^N-1$ current signals to the $2^N-1$ amplifier modules 3. Because conversion efficiency of the $2^N-1$ photodetectors 2 is different, strength of the converted $2^N-1$ current signals is also different. It may be set according to a requirement that the strength of the $2^N-1$ current signals decreases progressively according to the preset proportion. This, for example, may include: an intensity of a current signal obtained by conversion by an $n^{th}$ (of the $2^N-1$ photodetectors 2 shown in FIG. 2, a first photodetector 2 to a $(2^N-1)^{th}$ photodetector 2 are respectively arranged from top to bottom along a vertical direction shown in FIG. 2) photodetector 2 of the $2^N-1$ photodetectors 2 is I/(n−k), where k is a coefficient, k is a positive number, n is a positive integer, an initial value of n is 1, and n is less than or equal to $2^N-1$. That is, intensities of the $2^N-1$ current signals are I/(1−k), I/(2−k), I(3−k), . . . , and I($2^N-1-k$) respectively. The photodetector in this embodiment may be a photodiode.

The amplification multiples of the $2^N-1$ amplifier modules 3 are the same, and may set to Δ, where a value of Δ is one $(2^N)^{th}$ of a reference voltage. After the $2^N-1$ photodetectors 2 input the $2^N-1$ current signals to the foregoing $2^N-1$ amplifier modules 3, the $2^N-1$ output voltages outputted by the $2^N-1$ amplifier modules 3 are ΔI(1−k), ΔI(2−k), ΔI/(3−k), . . . , and ΔI/($2^N-1-k$) respectively, and then the $2^N-1$ amplifier modules 3 separately input the $2^N-1$ output voltages to the encoder 4.

A decision voltage is preset in the encoder 4. For example, the decision voltage may be ΔI(1−k).

The encoder separately (concurrently) compares the $2^N-1$ output voltages with the decision voltage, and obtains the decision results of $2^N-1$ input ends of the encoder 4 according to the comparison results. A specific step is identical to a step of obtaining the decision results of the $2^N-1$ input ends of the encoder 4 in the first implementation manner, and details are not described.

The encoder 4 obtains the N-bit digital signal by calculation by using the decision results of the $2^N-1$ input ends and outputs the N-bit digital signal.

For example, in this embodiment, it is set that k=0, and the decision voltage is ΔI, intensities of the $2^N-1$ current signals are I, I/2, I/3, . . . , and I/($2^N-1$) respectively. Because the amplification multiples of the $2^N-1$ amplifier modules are Δ, the $2^N-1$ output voltages outputted by the $2^N-1$ amplifier modules are ΔI, ΔI/2, ΔI/3, . . . , and ΔI/($2^N-1$) respectively. The $2^N-1$ output voltages ΔI, ΔI/2, ΔI/3, . . . , and ΔI/($2^N-1$) are separately compared with ΔI, and it may be concluded that only the output voltage of the first amplifier module is not less than the decision voltage. Therefore, the obtained decision results of the $2^N-1$ input ends of the encoder 4 are 1, 0, 0, 0, . . . , and 0 respectively. In this case, a quantity of 1 in the $2^N-1$ decision results is 1, and the N-bit digital signal that is obtained by the encoder by calculation according to the $2^N-1$ decision results and that is outputted by the encoder is 00 . . . 001.

If the inputted analog optical signal changes, and it is assumed that an intensity of a photocurrent signal generated by each photodetector changes to 2I, the output voltage of the first amplifier module and an output voltage of a second amplifier module are not less than a decision level. In this case, the quantity of 1 in the $2^N-1$ decision results is 2, and the N-bit digital signal outputted by the encoder 4 is 00 . . . 010 in this case.

In addition, k may be another value. For example, it may be set that k=0.5, and the decision voltage is ΔI/0.5, intensities of the $2^N-1$ current signals are I/0.5, I/1.5, I/2.5, . . . , and I/($2^N-1.5$) respectively, and the output voltages of the $2^N-1$ amplifier modules are IΔ/0.5, IΔ/1.5, IΔ/2.5, . . . , and IΔ/($2^N-1.5$). In addition, k may be another value, for example, 0.9, or 0.001. A specific value of k needs to be adjusted according to power of the inputted analog optical signal, so as to select a proper decision voltage for the analog optical signal on which A/D conversion needs to be performed, thereby ensuring a more accurate decision. A step of converting the analog optical signal into a digital signal when k is another value is the same as that when k=0, and details are not described.

An analog optical signal can be directly converted into a digital signal by using the foregoing method.

In a third implementation manner, a comparator function may be implemented by using the M photodetectors 2 of same conversion efficiency, and the M amplifier modules 3 of a same amplification multiple, and by setting that power of M optical signals outputted by the beam splitter 1 after light splitting decreases progressively according to a preset proportion.

Specifically, the beam splitter 1 is configured to split an inputted analog optical signal into the M optical signals, and output each optical signal to a corresponding photodetector 2. The power of the M optical signals decreases progressively from a first optical signal to an $M^{th}$ optical signal according to the preset proportion.

The photodetector 2 is configured to convert the inputted optical signal into a current signal, and input the current signal to a corresponding amplifier module 3. Conversion efficiency of the M photodetectors 2 is equal.

The amplifier module 3 is configured to generate an output voltage according to the inputted current signal, and output the output voltage to a corresponding input end of the encoder. Amplification multiples of the M amplifier modules 3 are equal.

The encoder 4 is configured to compare M output voltages with a decision voltage, and output a digital signal according to comparison results.

For example, the analog to digital converter is an N-bit precision analog to digital converter, M=$2^N-1$, and N is a positive integer. The analog to digital converter provided in the foregoing third implementation manner is described in detail by using the following example.

After the analog optical signal is inputted to the beam splitter 1, the beam splitter 1 splits the analog optical signal into the $2^N-1$ optical signals, and separately outputs the $2^N-1$ optical signals to the $2^N-1$ photodetectors 2. It may be set, by configuring the beam splitter 1, that the power of the $2^N-1$ optical signals decreases progressively according to the preset proportion. For example, it may be set that power of an $n^{th}$ (of the $2^N-1$ optical signals shown in FIG. 2, a first optical signal to a $(2^N-1)^{th}$ optical signal are respectively arranged from top to bottom along a vertical direction shown in FIG. 2) optical signal of the $2^N-1$ optical signals is p/n−k, where k is a coefficient, k is a positive number, n is a positive integer, an initial value of n is 1, and n is less than or equal to $2^N-1$. That is, the power of the $2^N-1$ optical signals is p/(1−k), p/(2−k), p/(3−k), . . . , and p/($2^N-1-k$) respectively. The beam splitter 1 may be implemented by using a silicon waveguide or a silicon dioxide waveguide, or may be implemented in another manner.

Because a current signal obtained by conversion by a photodetector 2 is equal to power of an inputted optical signal multiplied by conversion efficiency of the photodetector 2, strength of the current signal obtained by conversion by the photodetector 2 is directly proportional to the power of the inputted optical signal. Therefore, current signals obtained by conversion by the $2^N-1$ photodetectors 2 are I/(1−k), I/(2−k), I/(3−k), . . . , and I/($2^N-1-k$) respectively. The photodetector in this embodiment may be a photodiode.

The amplification multiples of the $2^N-1$ amplifier modules 3 are the same, and may set to Δ, where a value of Δ is one $(2^N)^{th}$ of a reference voltage. After the $2^N-1$ photodetectors 2 input the $2^N-1$ current signals to the foregoing $2^N-1$ amplifier modules 3, the $2^N-1$ output voltages outputted by the $2^N-1$ amplifier modules 3 are ΔI/(1−k), ΔI/(2−k), $\Delta I/(3-k), \ldots,$ and $\Delta I/(2^N-1-k)$ respectively, and then the $2^N-1$ amplifier modules 3 separately input the $2^N-1$ output voltages to the encoder 4.

A decision voltage is preset in the encoder 4. For example, the decision voltage may be $\Delta I/(1-k)$.

The encoder then separately (concurrently) compares the $2^N-1$ output voltages with the decision voltage, and obtains the decision results of $2^N-1$ input ends of the encoder 4 according to the comparison results. A specific step is identical to a step of obtaining the decision results of the $2^N-1$ input ends of the encoder 4 in the first implementation manner, and details are not described.

Finally, the encoder 4 obtains the N-bit digital signal by calculation by using the decision results of the $2^N-1$ input ends and outputs the N-bit digital signal. A detailed step in which the encoder separately compares the $2^N-1$ output voltages with the decision voltage is identical to a step in the second implementation manner, and details are not described.

Figure 4:
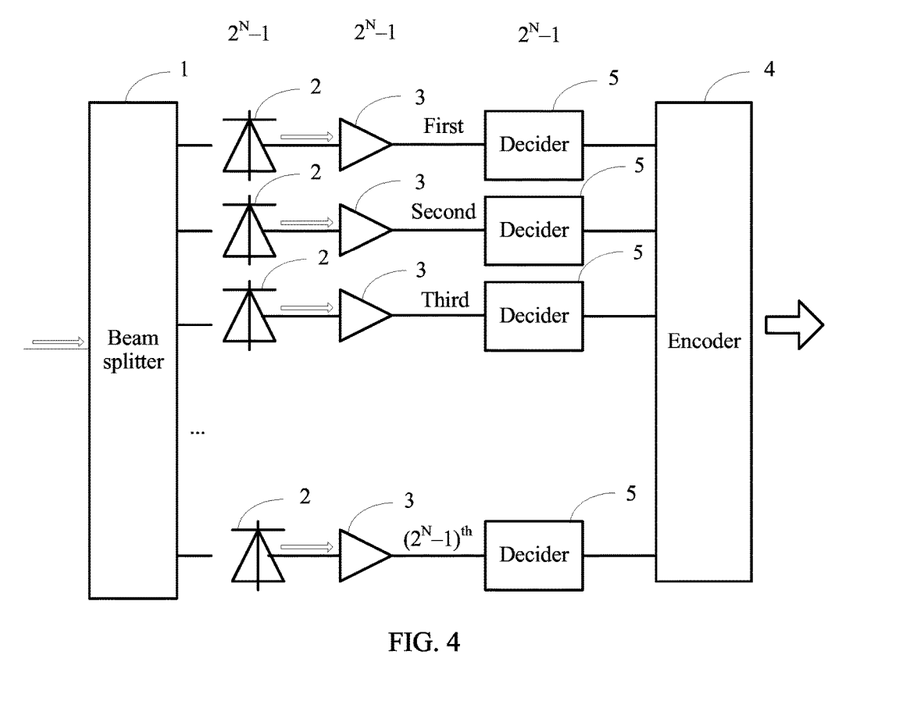
FIG. 4 is a schematic structural diagram of another analog to digital converter according to an embodiment of the present invention.

In a fourth implementation manner, power of M optical signals outputted by the beam splitter 1 after light splitting is the same, conversion efficiency of the M photodetectors 2 is the same, and amplification multiples of the M amplifier modules 3 are the same, and a comparator function is implemented by adding M deciders between the M amplifier modules and the encoder. As shown in FIG. 4, each output end of the beam splitter 1 is corresponding to an input end of a photodetector 2, an output end of each photodetector 2 is connected to an input end of an amplifier module 3, an output end of each amplifier module 3 is connected to a decider 5, and an output end of each decider 5 is connected to an input end of the encoder 4.

Specifically, the beam splitter 1 is configured to split an inputted analog optical signal into the M optical signals, and output each optical signal to a corresponding photodetector 2. The power of the M optical signals is equal.

The photodetector 2 is configured to convert the inputted optical signal into a current signal, and input the current signal to a corresponding amplifier module 3. The conversion efficiency of the M photodetectors 2 is equal.

The amplifier module 3 is configured to generate an output voltage according to the inputted current signal, and output the output voltage to a corresponding decider 5. The amplification multiples of the M amplifier modules 3 are equal.

Decision voltages are set in the M deciders 5, and the decision voltages of the M deciders increase progressively from a first decider to an $M^{th}$ decider according to a preset proportion. The decider 5 is configured to compare the inputted output voltage with a decision voltage of the decider 5, so as to obtain a decision result, and transmit the decision result to a corresponding input end of the encoder.

The encoder 4 is configured to generate a digital signal according to M decision results.

For example, the analog to digital converter is an N-bit precision analog to digital converter, $M=2^N-1$, and N is a positive integer. The analog to digital converter provided in the foregoing fourth implementation manner is described in detail by using the following example.

After the analog optical signal is inputted to the beam splitter 1, the beam splitter 1 splits the analog optical signal into the $2^N-1$ optical signals of equal power, and separately outputs the $2^N-1$ optical signals to the $2^N-1$ photodetectors 2. The beam splitter 1 may be implemented by using a silicon waveguide or a silicon dioxide waveguide, or may be implemented in another manner.

Because the conversion efficiency of the $2^N-1$ photodetectors 2 is identical, strength of $2^N-1$ current signals obtained by conversion by the $2^N-1$ photodetectors 2 according to the $2^N-1$ optical signals is the same. It is assumed that the intensity of the $2^N-1$ current signals are I, and the photodetector in this embodiment may be a photodiode.

The amplification multiples of the $2^N-1$ amplifier modules 3 are the same, and may set to $\Delta$, where a value of $\Delta$ is one $(2^N)^{th}$ of a reference voltage. After the $2^N-1$ photodetectors 2 input the $2^N-1$ current signals to the foregoing $2^N-1$ amplifier modules 3, $2^N-1$ output voltages outputted by the $2^N-1$ amplifier modules 3 are $\Delta I$, and then the $2^N-1$ amplifier modules 3 separately input the $2^N-1$ output voltages to the $2^N-1$ deciders 5.

It may be set, by using the $2^N-1$ deciders 5, that the decision voltages of the $2^N-1$ deciders 5 increase progressively according to the preset proportion. For example, it may be set that a decision voltage of an $n^{th}$ (of the $2^N-1$ deciders shown in FIG. 4, a first decider to a $(2^N-1)^{th}$ decider are respectively arranged from top to bottom along a vertical direction shown in FIG. 4) decider of the $2^N-1$ deciders 5 is $(n-k)\Delta I$, where k is a coefficient, k is a positive number, n is a positive integer, an initial value of n is 1, and n is less than or equal to $2^N-1$. That is, the decision voltages of the $2^N-1$ deciders 5 are $(1-k)\Delta I$, $(2-k)\Delta I$, $(3-k)\Delta I$, ..., and $(2^N-1-k)\Delta I$ respectively.

The $2^N-1$ deciders 5 separately compare the $2^N-1$ output voltages with the decision voltages of the $2^N-1$ deciders 5, so as to obtain the multiple decision results, and transmit the multiple decision results to the encoder 4.

The encoder 4 obtains the N-bit digital signal by calculation by using the decision results of $2^N-1$ input ends and outputs the N-bit digital signal.

For example, in this embodiment, it is set that k=0, and the decision voltages of the $2^N-1$ deciders are $\Delta I$, $2\Delta I$, $3\Delta I$, ..., and $(2^N-1)\Delta I$ respectively. Because the intensities of the $2^N-1$ current signal are I, and the amplification multiples of the $2^N-1$ amplifier modules are $\Delta$, the $2^N-1$ output voltages outputted by the $2^N-1$ amplifier modules are $\Delta I$. The $2^N-1$ output voltages $\Delta I$ are separately compared with the decision voltages $\Delta I$, $2\Delta I$, $3\Delta I$, ..., and $(2^N-1)\Delta I$, and it may be concluded that the output voltage of the first amplifier module is not less than the decision voltage. Therefore, the obtained decision results of the $2^N-1$ input ends of the encoder 4 are 1, 0, 0, 0, ..., and 0 respectively. In this case, a quantity of 1 in the $2^N-1$ decision results is 1, and the N-bit digital signal that is obtained by the encoder by calculation according to the $2^N-1$ decision results and that is outputted by the encoder is 00 ... 001.

If the inputted analog optical signal changes, and it is assumed that an intensity of a photocurrent signal generated by each photodetector changes to 2I, the output voltage of the first amplifier module and an output voltage of a second amplifier module are not less than a decision level. In this case, the quantity of 1 in the $2^N-1$ decision results is 2, and the N-bit digital signal outputted by the encoder 4 is 00 ... 010 in this case.

In addition, k may be another value. For example, it may be set that k=0.5, and the decision voltages are $0.5\Delta I$, $1.5\Delta I$, $2.5\Delta I$, ..., and $(2^N-1.5)\Delta I$ respectively. In addition, k may be another value, for example, 0.9, or 0.001. A specific value of k needs to be adjusted according to power of the inputted analog optical signal, so as to select a proper decision voltage for the analog optical signal on which A/D conversion needs to be performed, thereby ensuring a more accurate decision. A step of converting the analog optical signal into a digital signal when k is another value is the same as that when k=0, and details are not described.

Certainly, the decision voltages of the foregoing M deciders 5 may be identical. In this case, a comparator may be implemented by setting at least one of the following manners: the amplification multiples of the M amplifier modules decrease progressively according to a preset proportion, the conversion efficiency of the M photodetectors 2 decreases progressively according to a preset proportion, or the power of the M optical signals outputted from M output ends of the beam splitter decreases progressively according to a preset proportion. Methods for implementing these manners are respectively the same as that of the foregoing first implementation manner, the second implementation manner, and the third implementation manner, and details are not described.

An analog optical signal can be directly converted into a digital signal by using the foregoing method.

Compared with the prior art in which an analog optical signal needs to be first converted into an analog electrical signal before electrical analog to digital conversion (ADC) is performed, in the embodiments of the present invention, an analog optical signal can be directly converted into a digital signal, and analog to digital conversion is implemented by using an all-optical loop. This gets rid of an inherent limitation from a conventional electrical signal sampling head, thereby greatly improving an ADC rate.

Figure 5:
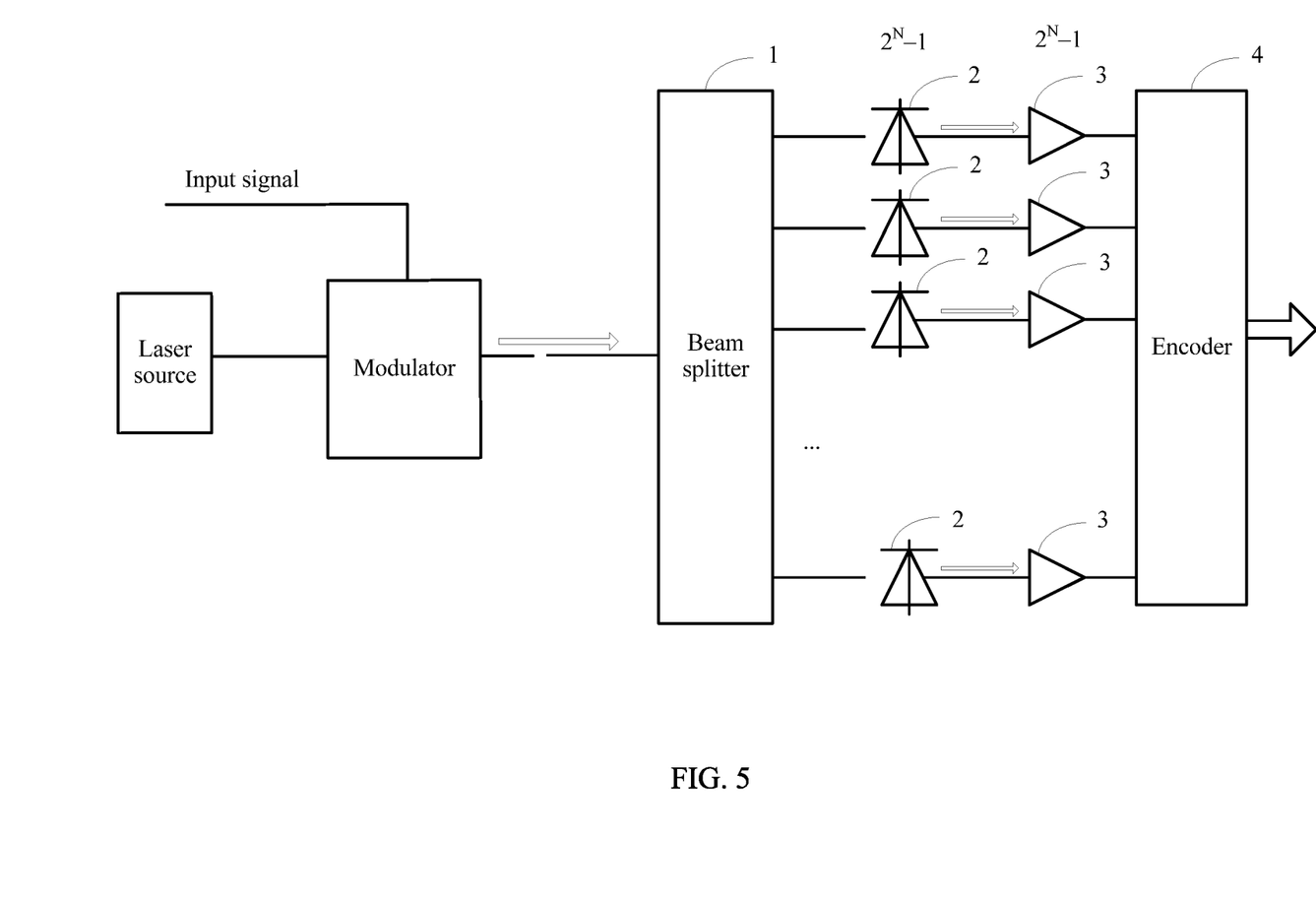
FIG. 5 is a schematic structural diagram of still another analog to digital converter according to an embodiment of the present invention.

In addition, in addition to directly converting an optical signal into a digital signal, the optical to electrical and analog to digital converter provided in the embodiments of the present invention can be applied to a scenario in which an analog electrical signal is converted into a digital signal. This improves a conversion rate in the analog electrical signal scenario. A method for converting the analog electrical signal into the digital signal specifically includes: The analog electrical signal is first inputted to a modulator (for example, an electro-absorption modulator), and is converted into an analog optical signal, and then the analog optical signal is outputted to the beam splitter 1. For a processing process after the analog optical signal is inputted to the beam splitter 1, reference may be made to the foregoing embodiments. The foregoing modulator may be a modulator including a laser source (for example, a commonly-used Mach-Zehnder modulator) shown in FIG. 5, or may be a laser source with an internal modulation function shown in FIG. 6.

Figure 6:
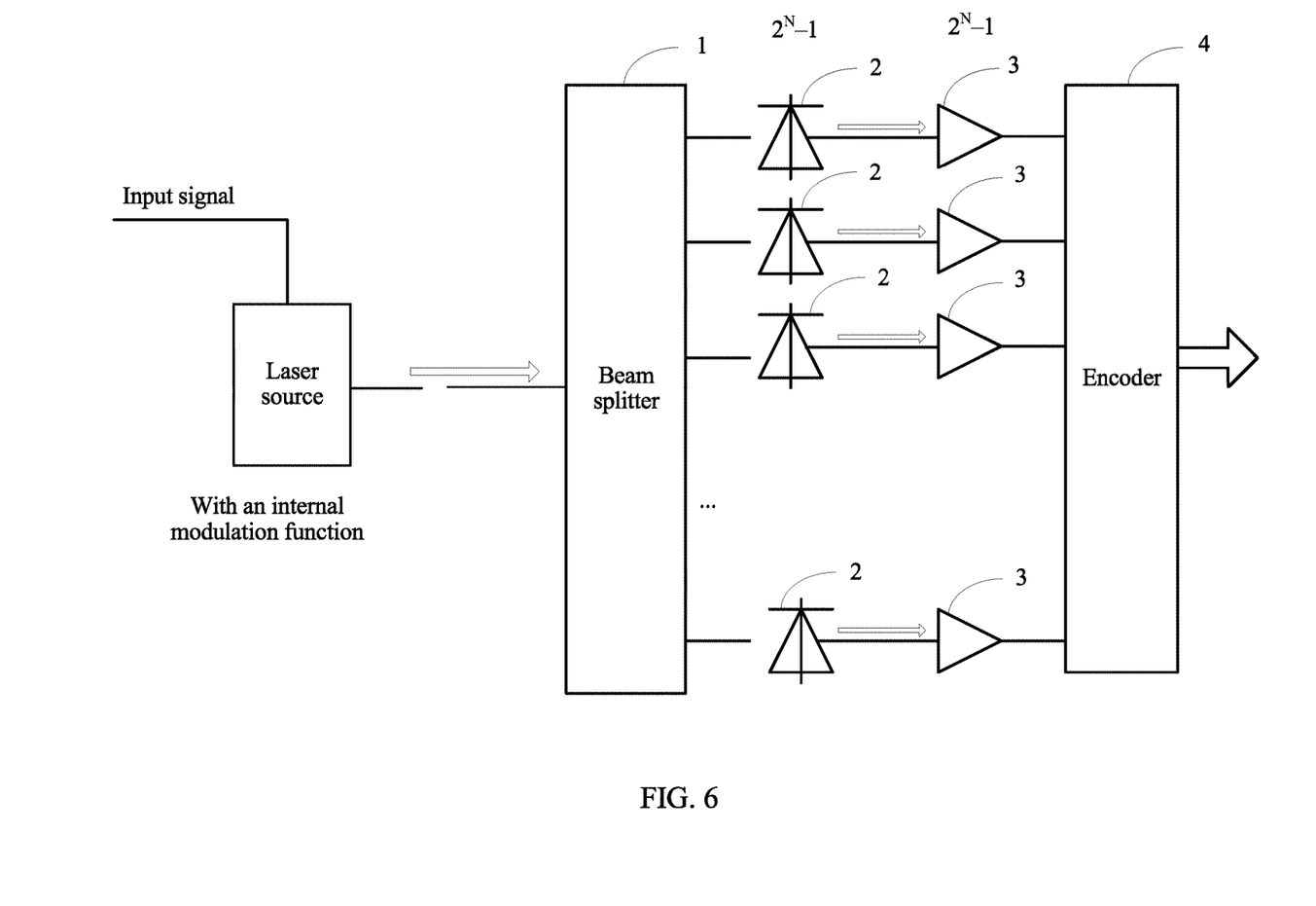
FIG. 6 is a schematic structural diagram of yet another analog to digital converter according to an embodiment of the present invention.
Figure 7:
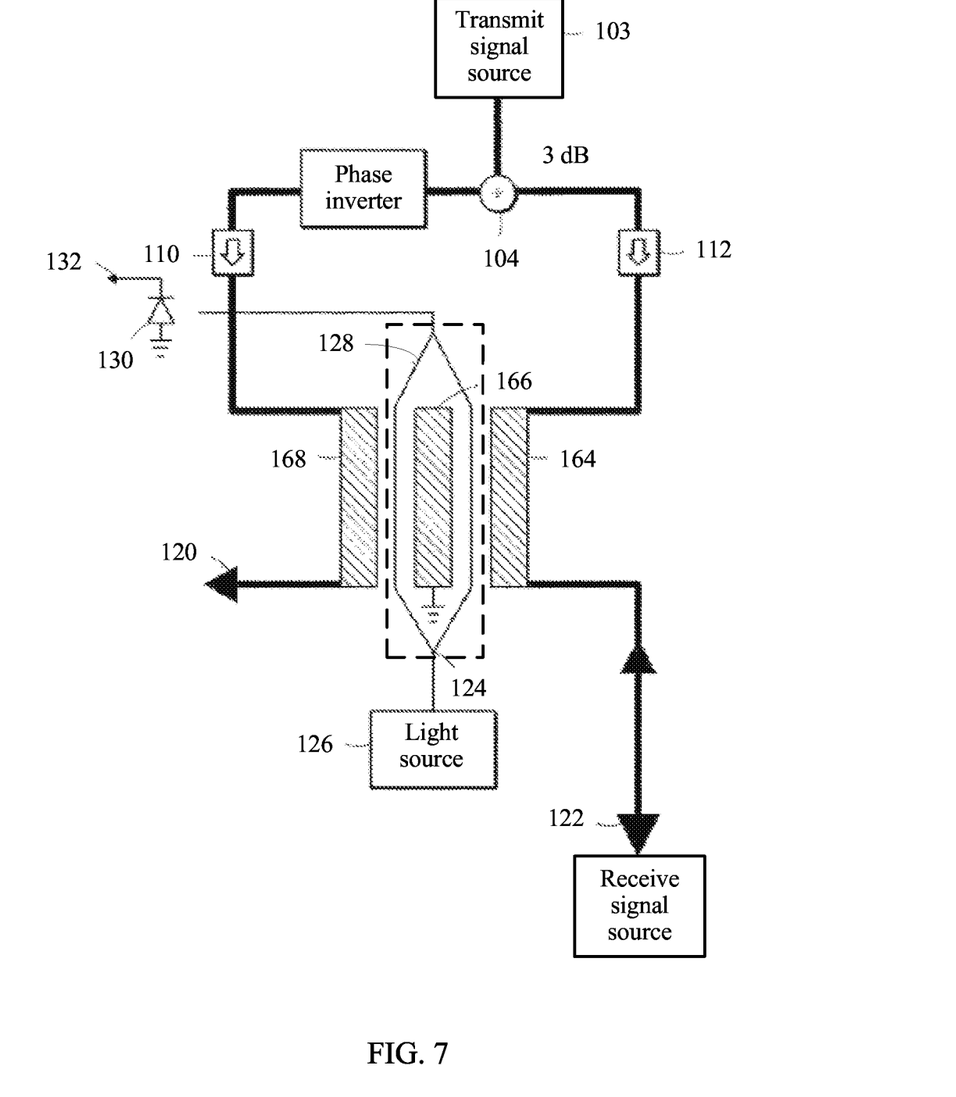
FIG. 7 is a schematic structural diagram of a modulator in the prior art.

For example, the foregoing Mach-Zehnder modulator is used as an example. The Mach-Zehnder modulator is a high-isolation transmit/receive isolator recently put forward in the industry. As shown in FIG. 7, a principle of the Mach-Zehnder modulator is as follows:

Light emitted by a light source 126 is split into two beams of light of equal power by a beam splitter 124, and the two beams of light enter a left arm and a right arm (the two arms in FIG. 6 are drawn along a vertical direction, and therefore are referred to as the left arm and the right arm, and the two arms are also usually drawn along a horizontal direction, and therefore may be referred to as an upper arm and a lower arm) of the Mach-Zehnder modulator. The two beams of light are combined into one beam in a beam combiner 128. During beam combining, if a phase difference between light in the left arm and light in the right arm is zero degrees, constructive interference occurs, and in this case, light power after the beam combining is the highest. If the phase difference is 180 degrees, output light power is 0. Different phase differences indicate different output light power. A spindle line in a dotted line box in FIG. 6 represents an optical path.

164, 166, and 168 are electrodes. A voltage difference between the electrode 164 and the electrode 166 generates an electric field between the electrode 164 and the electrode 166. This changes a refractive index of the light in the right arm, thereby changing a phase of the light transmitted in the right arm. Likewise, a voltage difference between the electrode 168 and the electrode 166 generates an electric field between the electrode 168 and the electrode 166. This changes a refractive index of the light in the left arm, thereby changing a phase of the light transmitted in the left arm. Output power of the Mach-Zehnder modulator can be affected by using this principle and by controlling a voltage on the electrode 164 and a voltage on the electrode 168.

Specifically, a transmit signal (an analog electrical signal) of a transmit signal source 103 is split into two beams by a 3 dB beam splitter 104 (3 dB in FIG. 6 means that a beam splitting ratio of the beam splitter 104 is 1:1, that is, power of signals of two output ports is equal). A signal on the right passes through the electrode 164, and is transmitted to an antenna 122. A signal on the left is transmitted to the electrode 168. A signal monitoring port 120 is configured to connect to a transmit signal monitoring apparatus. When the transmit signal of the transmit signal source 103 is at a positive level, because the signal on the left is at an opposite level, there is a negative level on the electrode 168. Because the electrode 166 is connected to a ground, an electric field direction between the electrode 168 and the electrode 166 is from right to left. A level on the electrode 164 is a positive level, and therefore, the electric field between the electrode 164 and the electrode 166 is also from right to left. In this way, directions of voltages in the two arms and magnitudes of the voltages in the two arms of the Mach-Zehnder modulator are the same, and phase changes on the two arms are also the same. It may be learned that a voltage of the transmit signal of the transmit signal source 103 imposes no impact on an output end 132 of the Mach-Zehnder modulator in this case. Likewise, when the transmit signal of the transmit signal source 103 is at a negative level, there is no impact either, that is, the transmit signal of the transmit signal source 103 theoretically does not crosstalk to the output port 132. However, a receive signal received by a receive signal source 122 is transmitted only to the electrode 164. Output of the Mach-Zehnder modulator varies with a change of the receive signal received by the receive signal source 122. The receive signal received by the receive signal source 122 is transmitted to the output end 132 by using this method. An isolator no and an isolator 112 are configured to prevent the receive signal or a reflected signal from entering 103 and affecting a transmitter.

However, in the prior art shown in FIG. 6, a photodetector 130 needs to be set, so as to convert an optical signal into an analog electrical signal, and output the analog electrical signal from the output end 132. An electrical high-speed ADC needs to be set following the output end 132, for example, the ADC shown in FIG. 1, so as to convert the received analog electrical signal into a digital signal. However, the ADC shown in FIG. 1 may not meet an ADC conversion rate requirement in the foregoing scenario because of a limitation from a circuit itself. The optical to electrical and analog to digital converter provided in the embodiments of the present invention can directly convert an optical signal into a digital signal, and can meet the ADC conversion rate requirement in the foregoing scenario. Therefore, there is no need to set the photodetector 130 shown in FIG. 6, and an optical signal obtained by means of beam combining by the beam combiner 128 may be directly inputted to the optical to electrical and analog to digital converter provided in the embodiments of the present invention, thereby meeting a service need.

In conclusion, the embodiments of the present invention provide an analog to digital converter, including a beam splitter, M photodetectors, M amplifier modules corresponding to the M photodetectors, and an encoder. Each output end of the beam splitter is corresponding to an input end of a photodetector, an output end of each photodetector is connected to an input end of an amplifier module, and an output end of each amplifier module is connected to an input end of the encoder. The beam splitter is configured to split an inputted analog optical signal into M optical signals, and output each optical signal to a corresponding photodetector. The photodetector is configured to convert the inputted optical signal into a current signal, and input the current signal to a corresponding amplifier module. The amplifier module is configured to generate an output voltage according to the inputted current signal, and output the output voltage to a corresponding input end of the encoder. A comparator may be implemented by setting at least one of power of output signals of the beam splitter, conversion efficiency of the M photodetectors, amplification multiples of the M amplifier modules, or M different decision voltages, so that the encoder outputs a digital signal according to decision results of comparisons between M output voltages and the decision voltages. Compared with the prior art in which an analog optical signal needs to be first converted into an analog electrical signal before electrical ADC is performed, in the embodiments of the present invention, an analog optical signal can be directly converted into a digital signal, and analog to digital conversion is implemented by using an all-optical loop. This gets rid of an inherent limitation from a conventional electrical signal sampling head, thereby greatly improving an ADC rate.

Finally, it should be noted that the foregoing embodiments are merely intended for describing the technical solutions of the present embodiments, but not for limiting the present embodiments. Although the present embodiments are described in detail with reference to the foregoing embodiments, a person of ordinary skill in the art should understand that they may still make modifications to the technical solutions described in the foregoing embodiments or make equivalent replacements to some or all technical features thereof, without departing from the scope of the technical solutions of the embodiments of the present invention.

What is claimed is:

1. An analog to digital converter, comprising:
a beam splitter, M photodetectors, M amplifier modules corresponding to the M photodetectors, and an encoder, wherein output ends of the beam splitter correspond to input ends of the M photodetectors, wherein output ends of the M photodetectors are connected to input ends of the M amplifier modules, and wherein output ends of the M amplifier modules are connected to input ends of the encoder;
wherein the beam splitter is configured to split an analog optical signal into M optical signals, and output optical signals of the M optical signals to a corresponding photodetectors of the M photodetectors;
wherein the M photodetectors are configured to convert the M optical signals into M current signals, and output the M current signals to a corresponding amplifier modules of the M amplifier modules;
wherein the M amplifier modules are configured to generate M output voltages according to the M current signals, and output the M output voltages to a corresponding input ends of the encoder; and
wherein the encoder is configured to compare the M output voltages with a decision voltage, to obtain M decision results, and generate a digital signal according to the M decision results; and
wherein power of the M optical signals decreases progressively from a first optical signal to an $M^{th}$ optical signal according to a first preset proportion, wherein conversion efficiency of the M photodetectors decreases progressively from a first photodetector to an $M^{th}$ photodetector according to a second preset proportion, and wherein amplification multiples of the M amplifier modules decrease progressively from a first amplifier module to an $M^{th}$ amplifier module according to a third preset proportion, so the M output voltages inputted to the encoder decrease progressively from a first output voltage to an $M^{th}$ output voltage according to a fourth preset proportion.

2. The analog to digital converter according to claim 1, wherein the analog to digital converter is an N-bit precision analog to digital converter, wherein M is equal to $2^N-1$, wherein the digital signal is of N bits, and wherein M and N are positive integers.

3. The analog to digital converter according to claim 1, wherein an amplification multiple of an $n^{th}$ amplifier module of the M amplifier modules is $\Delta/(n-k)$; and
wherein an output voltage of the $n^{th}$ amplifier module of the M amplifier modules is $\Delta I/(n-k)$, wherein I is a strength of the M current signals outputted by the M photodetectors, and wherein strengths of the M current signals outputted by the M photodetectors are equal;
wherein the decision voltage is $\Delta I/(1-k)$; and
wherein a value of $\Delta$ is one $(2^N)^{th}$ of a reference voltage, wherein k is a coefficient,
wherein k is a positive number, wherein n is a positive integer, wherein an initial value of n is 1, and wherein n is less than or equal to M.

4. The analog to digital converter according to claim 1, wherein a conversion efficiency of an $n^{th}$ photodetector of the M photodetectors is $1/(n-k)$;
wherein a strength of a current signal outputted by the $n^{th}$ photodetector of the M photodetectors is $I/(n-k)$, wherein powers of the M optical signals being equal; and
wherein an output voltage of an $n^{th}$ amplifier module of the M amplifier modules is $\Delta I/(n-k)$, wherein amplification multiples of the M amplifier modules being equal;
wherein the decision voltage is $\Delta I/(1-k)$; and
wherein $\Delta$ is an amplification multiple of the M amplifier modules, wherein a value of $\Delta$ is one $(2^N)^{th}$ of a reference voltage, wherein k is a coefficient, wherein k is a positive number, wherein n is a positive integer, wherein an initial value of n is 1, and wherein n is less than or equal to M.

5. The analog to digital converter according to claim 1, wherein a power of an $n^{th}$ optical signal of the M optical signals is $p/(n-k)$;
an intensity of a current signal outputted by an $n^{th}$ photodetector of the M photodetectors is $I/(n-k)$, wherein conversion efficiencies of the M photodetectors and equal;
wherein an output voltage of an $n^{th}$ amplifier module of the M amplifier modules is $\Delta I/(n-k)$, wherein the amplification multiples of the M amplifier modules are equal; wherein the decision voltage is $\Delta I/(1-k)$; and wherein $\Delta$ is an amplification multiple of the M amplifier modules, wherein a value of $\Delta$ is one $(2^N)^{th}$ of a reference voltage, wherein k is a coefficient, wherein k is a positive number, wherein n is a positive integer, wherein an initial value of n is 1, and wherein n is less than or equal to M.

6. The analog to digital converter according to claim 1, wherein the encoder is further configured to:

compare the M output voltages inputted from M input ends with the decision voltage, to obtain the M decision results, wherein values of the M decision results comprise a first value or a second value;

count a quantity of decision results whose values are the first value in the M decision results; and generate the digital signal according to the quantity of decision results whose values are the first value in the M decision results, wherein the digital signal has N bits.

7. The analog to digital converter according to claim 6, wherein the encoder is further configured to:

determine that a decision result of an $n^{th}$ input end is the first value, in response to an output voltage of an $n^{th}$ amplifier module inputted from an $n^{th}$ input end being greater than or equal to the decision voltage; and determine that a decision result of the $n^{th}$ input end is the second value, wherein the $n^{th}$ amplifier module is any one of the M amplifier modules, and the $n^{th}$ input end is an input end corresponding to the $n^{th}$ amplifier module if the output voltage of the $n^{th}$ amplifier module is less than the decision voltage.

8. The analog to digital converter according to claim 6, wherein the analog to digital converter further comprises a modulator, wherein an output end of the modulator is connected to an input end of the beam splitter, and wherein the modulator is configured to convert an analog electrical signal into the analog optical signal, and input the analog optical signal to the beam splitter.

9. The analog to digital converter according to claim 8, wherein the modulator comprises a laser source.

10. The analog to digital converter according to claim 8, wherein the modulator comprises a laser source with an internal modulation function.

11. The analog to digital converter according to claim 1, wherein the M amplifier modules comprise transimpedance amplifiers.

12. An analog to digital converter, wherein the analog to digital converter comprises:

a beam splitter, M photodetectors, M amplifier modules corresponding to the M photodetectors, M deciders corresponding to the M amplifier modules, and an encoder; wherein output ends of the beam splitter correspond to input ends of the M photodetectors, wherein output ends of the M photodetectors are connected to input ends of the M amplifier modules, wherein output ends of the M amplifier modules are connected to the M decider, and wherein output ends of the M deciders are connected to input ends of the encoder;

wherein the beam splitter is configured to split an analog optical signal into M optical signals, and output the M optical signals to a corresponding photodetectors, wherein powers of the M optical signals are equal;

wherein the M photodetectors are configured to convert the M optical signals into current signals, and input the current signals to a corresponding amplifier modules, wherein conversion efficiencies of the M photodetectors are equal;

wherein the M amplifier modules are configured to generate M output voltages according to the current signals, and output the M output voltages to corresponding deciders, wherein amplification multiples of the M amplifier modules are equal;

wherein decision voltages are set in the M deciders, wherein the decision voltages of the M deciders progressively decrease from a first decider to an $M^{th}$ decider according to a preset proportion, and wherein the M deciders are configured to compare the M output voltages with decision voltages of the M deciders, to obtain M decision results, and transmit the M decision results to corresponding input ends of the encoder;

wherein the encoder is configured to generate a digital signal according to the M decision results; and wherein the analog to digital converter is an N-bit precision analog to digital converter, wherein $M=2^N-1$, wherein the digital signal has N bits, and wherein M and N are positive integers.

13. The analog to digital converter according to claim 12, wherein a decision voltage of an $n^{th}$ decider of the M deciders is $(n-k)\Delta I$, wherein I is strength of M currents, wherein $\Delta$ is the amplification multiples of the M amplifier modules, wherein $\Delta I$ is a magnitude of M output voltages, wherein $\Delta$ is one $(2^N)^{th}$ of a reference voltage, wherein k is a coefficient, wherein k is a positive number, wherein n is a positive integer, wherein an initial value of n is 1, and wherein n is less than or equal to M.

14. The analog to digital converter according to claim 12, wherein values of an M decision results comprise a first value or a second value, and wherein the encoder is further configured to:

count a quantity of decision results whose value is the first value in the M decision results; and generate the digital signal according to the quantity of decision results whose value is the first value in the M decision results, wherein the digital signal has N bits.

15. The analog to digital converter according to claim 14, wherein an $n^{th}$ decider is further configured to:

determine that a decision result of the $n^{th}$ decider is the first value, in response to an output voltage of an $n^{th}$ amplifier module being greater than or equal to a decision voltage of the $n^{th}$ decider; and determine that a decision result of the $n^{th}$ decider is the second value, in response to an output voltage of an $n^{th}$ amplifier module being less than the decision voltage of the $n^{th}$ decider, wherein the $n^{th}$ amplifier module is any one of the M amplifier modules, and wherein the $n^{th}$ decider is a decider corresponding to the $n^{th}$ amplifier module.

16. The analog to digital converter according to claim 12, wherein the M amplifier modules comprise transimpedance amplifiers.

17. The analog to digital converter according to claim 12, wherein the analog to digital converter further comprises a modulator, wherein an output end of the modulator is connected to an input end of the beam splitter, and wherein the modulator is configured to convert an analog electrical signal into the analog optical signal, and input the analog optical signal to the beam splitter.

18. The analog to digital converter according to claim 17, wherein the modulator comprises a modulator comprising a laser source.

19. The analog to digital converter according to claim 17, wherein the modulator comprises a laser source with an internal modulation function.

20. A method comprising:
- splitting, by a beam splitter of an analog to digital converter, an inputted analog optical signal into M optical signals;
- outputting, by the beam splitter, optical signals of the M optical signals to corresponding photodetectors of M photodetectors of the analog to digital converter;
- converting, by the M photodetectors, the M optical signals into current signals;
- outputting, by the M photodetectors, the current signals to corresponding amplifier modules of M amplifier modules of the analog to digital converter;
- generating, by the M amplifier modules, output voltages according to the current signals;
- outputting, by the M amplifier modules, the output voltages to corresponding input ends of an encoder of the analog to digital converter;
- comparing, by the encoder, the output voltages with a decision voltage, to obtain M decision results; and
- generate a digital signal according to the M decision results, wherein power of the M optical signals decreases progressively from a first optical signal to an $M^{th}$ optical signal according to a first preset proportion, wherein the analog to digital converter is an N-bit precision analog to digital converter, wherein M is equal to $2^N-1$, wherein the digital signal is of N bits, and wherein M and N are positive integers.

* * * * *